(12) United States Patent
Patel (10) Patent No.: US 9,044,394 B2
(45) Date of Patent: *Jun. 2, 2015

(54) BIOAVAILABILITY ENHANCEMENT DELIVERY COMPOSITION

(75) Inventor: Bhiku G. Patel, Chandler, AZ (US)

(73) Assignee: PruGen IP Holdings, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,331

(22) Filed: Nov. 30, 2011

(65) Prior Publication Data

US 2012/0252906 A1   Oct. 4, 2012

Related U.S. Application Data

(63) Continuation-in-part of application No. 12/906,419, filed on Oct. 18, 2010.

(51) Int. Cl.
| | |
|---|---|
| A61K 31/40 | (2006.01) |
| A61K 31/16 | (2006.01) |
| A61K 9/107 | (2006.01) |
| A61K 47/22 | (2006.01) |
| A61K 47/26 | (2006.01) |
| A61K 9/48 | (2006.01) |
| A61K 31/202 | (2006.01) |
| A61K 31/00 | (2006.01) |
| A61K 47/14 | (2006.01) |
| A61K 47/44 | (2006.01) |

(52) U.S. Cl.
CPC ............ *A61K 9/107* (2013.01); *A61K 47/22* (2013.01); *A61K 47/26* (2013.01); *A61K 9/4858* (2013.01); *A61K 31/202* (2013.01); *A61K 9/1075* (2013.01); *A61K 31/00* (2013.01); *A61K 47/14* (2013.01); *A61K 47/44* (2013.01)

(58) Field of Classification Search
USPC ................... 514/937, 408, 613, 615
See application file for complete search history.

(56) References Cited

U.S. PATENT DOCUMENTS

| | | | | |
|---|---|---|---|---|
| 6,121,234 | A * | 9/2000 | Benet et al. .................. 514/20.5 |
| 7,229,639 | B2 * | 6/2007 | Guillard et al. ............... 424/451 |
| 8,609,684 | B2 * | 12/2013 | Patel ............................. 514/289 |
| 8,937,081 | B2 * | 1/2015 | Patel ............................. 514/275 |
| 2003/0171264 | A1 | 9/2003 | Naicker et al. |
| 2005/0191343 | A1 | 9/2005 | Liang |
| 2006/0241175 | A1 * | 10/2006 | Schwarz et al. ............... 514/458 |
| 2007/0116758 | A1 * | 5/2007 | Dlugatch et al. ............... 424/464 |
| 2007/0166360 | A1 * | 7/2007 | Nakai et al. ................... 424/448 |
| 2011/0014282 | A1 | 1/2011 | De Vasconcelos |

FOREIGN PATENT DOCUMENTS

WO    WO 2009059717 A2 *   5/2009

OTHER PUBLICATIONS

Jiao, J., et al. Advanced Drug Delivery Reviews vol. 60, pp. 1663-1673. Published 2008.*
Ke, W-T et al., Journal of Controlled Release vol. 102, pp. 489-507. Published 2005.*
Park, H.M. et al., Biochemical and Biophysical Research Communications vol. 404, pp. 345-348. Published 2011.*
Ke, W-T. et al., Journal of Controlled Release vol. 102, pp. 489-507. Published 2005.*
Shen, H. et al., Journal of Pharmacy and Pharmacology vol. 58, pp. 1183-1191. Published 2006.*
Strickley, R. G. et al., Pharmaceutical Research vol. 21 pp. 201-230. Published 2004.*
Tween 80 Material Safety Data Sheet. Fisher Scientific. Published 1999.*
Ke et al., "Phyiscal characterizations of microemulsion systems using tocopheryl polyethylene glycol 1000 succinate (TPGS) as a surfactant for the oral delivery of protein drugs", Journal of Controlled Release, 2005, vol. 102, No. 2, pp. 489-507.
PCT/US2012/067409—International Search Report and Written Opinion dated Mar. 28, 2013.
PCT/US2012/067409—International Preliminary Report on Patentability dated Jun. 12, 2014.

* cited by examiner

*Primary Examiner* — Paul Zarek
*Assistant Examiner* — George W Kosturko
(74) *Attorney, Agent, or Firm* — Dale F. Regelman; Quarles & Brady LLP

(57) ABSTRACT

A composition for increasing the bioavailability of an active pharmaceutical ingredient ("API") in humans and animals, comprising a first water soluble surfactant having a cloud point greater than about 37° C., a second water soluble surfactant having a cloud point greater than about 37° C., wherein a mixture of the first surfactant and the second surfactant comprises a cloud point less than about 37° C.

1 Claim, 7 Drawing Sheets

BIOAVAILABILITY ENHANCEMENT DELIVERY COMPOSITION

CROSS REFERENCE TO RELATED APPLICATIONS

This Application is a Continuation-In-Part Application claiming priority from U.S. patent application having Ser. No. 12/906,419.

TECHNICAL FIELD

The present invention relates to the delivery of pharmaceuticals, nutraceuticals, vitamins, minerals, and other health therapeutics to humans or animals and, more particularly, to a composition that enhances the bioavailability of such agents.

BACKGROUND ART

Drug delivery is the method or process of administering an active pharmaceutical ingredient ("API") to achieve a therapeutic effect in humans or animals. The most common routes of administration include the peroral (through the mouth), topical, transmucosal (nasal, buccal/sublingual, vaginal, ocular and rectal), intra-muscular injection, arterio/venous injection, and inhalation.

Historically, pharmaceutical compositions have primarily consisted of simple, fast-acting chemical compounds. More recently, however, formulations that control the rate and period of drug delivery have become increasingly common and complex.

Current methods of drug delivery exhibit specific problems. For example, many API's potencies and therapeutic effects are limited or otherwise reduced because of the partial degradation that occurs before these APIs reach a desired target. This partial degradation can lead to a need for increased dosages in an attempt to reach a therapeutically acceptable level of available drug. This, in turn, can lead to an increase in side effects and adverse events.

Accordingly, there has been a long felt un-meet need to create an economical, stable drug delivery system that overcomes the need for heat and mechanical energy in its preparation, while at the same time increasing the bioavailability of APIs without altering the API itself, and while obtaining the goal of delivering the API at the lowest therapeutically acceptable level.

SUMMARY OF THE INVENTION

A composition for increasing the bioavailability of an active pharmaceutical ingredient ("API") in humans and animals is presented. The composition comprises a first water soluble surfactant having a cloud point greater than about 37° C., and a second water soluble surfactant having a cloud point greater than about 37° C., wherein a mixture of the first surfactant and the second surfactant comprises a cloud point less than about 37° C.

A composition for increasing the bioavailability of an active pharmaceutical ingredient ("API") in humans and animals formed by a process is presented. The process mixes a first water soluble surfactant having a cloud point greater than about 37° C. with a second water soluble surfactant having a cloud point greater than about 37° C., wherein the mixture of the first surfactant and the second surfactant comprises a cloud point less than about 37° C.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 7:
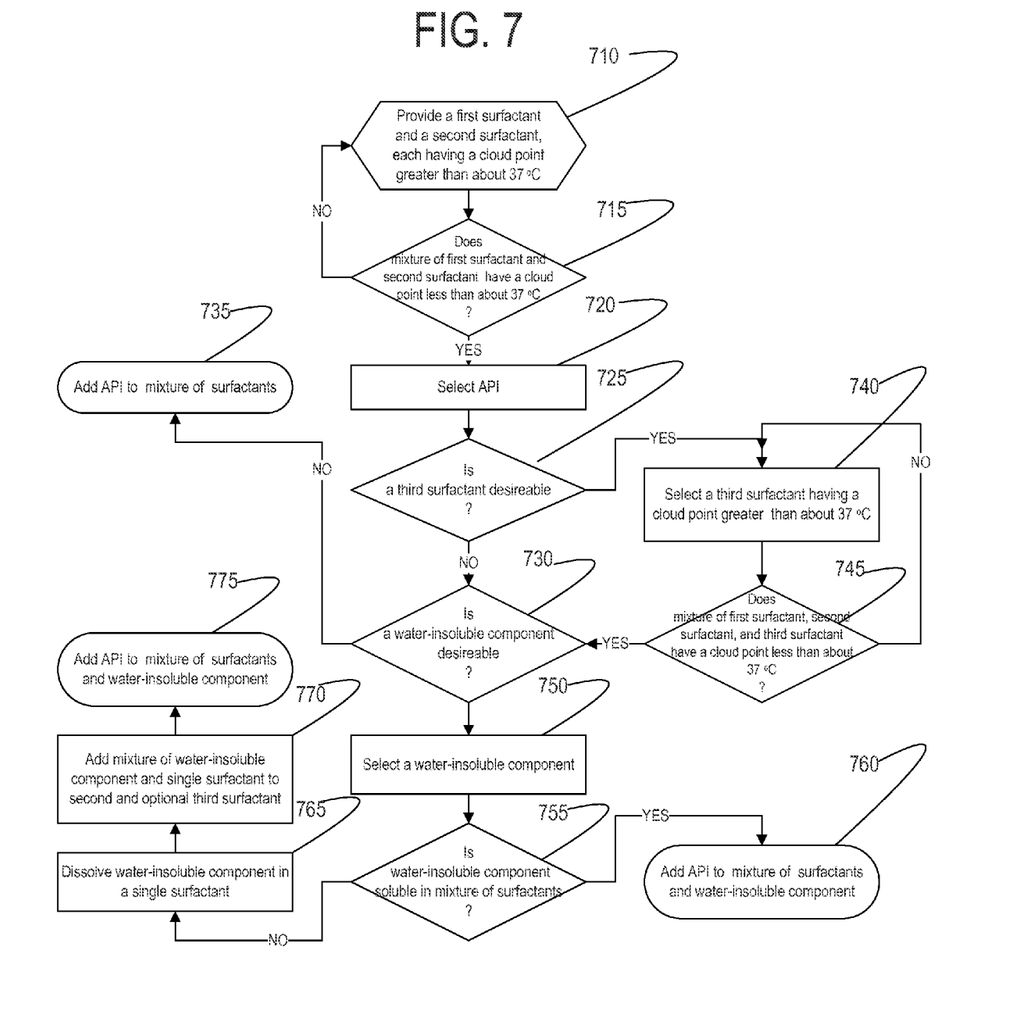
FIG. 7 summarizes the steps of Applicant's method to prepare his bioavailability enhancement delivery composition.

The schematic flow chart diagram included herein is generally set forth as logical flow-chart diagram (e.g., FIG. 7). As such, the depicted order and labeled steps are indicative of one embodiment of a presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention addresses the problem of drug bioavailability. Certain prior art pharmaceutical compositions comprise emulsions. Broadly speaking, an emulsion is a mixture of two or more immiscible liquids. Prior art drug delivery emulsion attempts have focused on macroemulsions comprising a plurality of API droplets disposed within a continuous aqueous phase. These prior art drug delivery compositions and methods also require heat and the input of considerable amounts of mechanical energy, which may be supplied by colloid mills, homogenizers, and ultrasonic generators. This raises the cost of preparation in a potentially less than desirable product.

Reference to pharmaceutical composition also includes nutraceutical, vitamin, mineral, and other health related compositions. More specifically, the present invention provides for the creation of a microemulsion wherein an API is solubilized within a discontinuous phase dispersed within a continuous aqueous phase. In certain embodiments, Applicant's microemulsion comprises a plurality of droplets comprising a mean diameter range of about 6 to about 100 nanometers and a narrow droplet size distribution.

To overcome prior art limitations in absorption and bioavailability of APIs, the Applicant has discovered that creating a microemulsion in turn creates an increase in API surface area per volume, thereby enabling greater gastrointestinal uptake of the API. Through the use of surfactants that do not create a permanent binding to the API, the bioavailability of the API is increased without altering the API itself. Importantly, the Applicant has discovered that such a microemulsion can be made without the prior art limitations of heat and mechanical energy, thereby creating a stable microemulsion that can be produced at lower cost due to the energy savings.

Cloud point is the temperature above which an aqueous solution of a water-soluble surfactant becomes turbid. Generally, nonionic surfactants show optimal effectiveness when used near or below their cloud point.

Cloud points are typically measured using 1% aqueous surfactant solutions. Cloud points range from 0° to 100° C. (32 to 212° F.), limited by the freezing and boiling points of water. Cloud points are characteristic of nonionic surfactants. Anionic surfactants (with negatively charged groups) are more water-soluble than nonionic surfactants and will typically have much higher cloud points (above 100° C.). The presence of other components in a formulation can depress or increase the solution's cloud point.

Cloud point is also a measure of the hydrophilic/lipophilic balance of a surface-active agent. When a surfactant can have its cloud point run in an aqueous solution, it is therefore a water soluble surface active agent; whereas, when a surfactant must have its cloud point run in an aqueous/solvent mixture, it is either water dispersible or oil soluble in character. Nonionic surface-active agents are less soluble at elevated temperatures in aqueous solutions and, therefore, exhibit a cloud point which varies with the hydrophilic/lipophilic balance of the nonionic surface-active agent.

Applicant's bioavailability enhancement delivery composition comprises a first surfactant and a second surfactant. In certain embodiments, the first surfactant comprises a cloud point greater than about 37° C. In certain embodiments, the second surfactant comprises a cloud point greater than about 37° C. In certain embodiments, both the first surfactant and the second surfactant individually comprise cloud points greater than about 37° C. In certain embodiments, the first surfactant comprises a HLB between about 14 and about 16. In certain embodiments, the second surfactant comprises a HLB between about 14 and about 16. In certain embodiments, both the first surfactant and the second surfactant individually comprises a HLB between about 14 and about 16.

In certain embodiments, Applicant's first surfactant comprises an ethoxylated carbohydrate moiety. In certain embodiments, Applicant's first surfactant comprises structure 1, wherein a, b, c, d, e, and f, are independently between 0 and about 20. R1, R2, R3, R4, R5, and R6, are selected from the group consisting of H and —CO—R7, wherein R7-COOH comprises a fatty acid. In certain embodiments, R7-COOH is selected from the group consisting of Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, and Docosahexaenoic acid.

Sorbitol, also known as glucitol, SORBOGEM and SORBO, is a sugar alcohol that the human body metabolizes slowly. It can be obtained by reduction of glucose, changing the aldehyde group to a hydroxyl group. Sorbitol is found in apples, pears, peaches, and prunes.

Sorbitan is a mixture of chemical compounds derived from the dehydration of sorbitol. The mixture can vary, but usually consists of 1,4-anhydrosorbitol, 1,5-anhydrosorbitol and 1,4,3,6-dianhydrosorbitol. Sorbitan is primarily used in the production of surfactants such as polysorbates.

Sorbitan esters (also known as Spans) are lipophilic non ionic surfactants that are used as emulsifying agents in the preparation of emulsions, creams, and ointments for pharmaceutical and cosmetic use. When used alone they produce stable water-in-oil emulsions but they are frequently used with a polysorbate in varying proportions to produce water-in-oil or oil-in-water emulsions or creams with a variety of different textures and consistencies. Sorbitan esters are also used as emulsifiers and stabilizers in food In certain embodiments, Applicant's first surfactant comprises a carbohydrate moiety. In certain embodiments, Applicant's first surfactant comprises a polysorbate having structure II, wherein w is between about 1 to about 20 and wherein x, y, and z, are each between 0 to about 20, and wherein R7 is defined hereinabove.

In certain embodiments, Applicant's first surfactant comprises polyoxyethylene sorbitan monooleate III.

$w + x + y + z = 20$

Compound III comprises an average molecular weight of about 1310, a micellar average molecular weight of about 79,900, an aggregation number of about 60, a cloud point of about 65° C., and a HLB of about 15.

In certain embodiments, Applicant's second surfactant comprises a vitamin moiety. In certain embodiments, Applicant's second surfactant comprises an ethoxylated vitamin composition. In certain embodiments, Applicant's second surfactant comprises an esterified Vitamin E composition. In certain embodiments, Applicant's second surfactant comprises tocopheryl polyethylene glycol succinate IV, wherein n is between about 10 to about 100.

Tocopheryl polyethylene glycol succinate comprises a cloud point of between 62° C. and about 75° C. at concentrations of from about 0.05 weight percent to about 15 weight percent, respectively. Tocopheryl polyethylene glycol succinate comprises a HLB of about 13.

In certain embodiments, Applicant's bioavailability enhancement delivery composition comprises a first surfactant comprising a cloud point greater than about 37° C., and a second surfactant comprising a cloud point greater than about 37° C., wherein a mixture of the first surfactant and the second surfactant comprises a cloud point less than 37° C.

Surfactant molecules self-associate in dilute aqueous solutions to generate aggregates of various types, shapes, and sizes such as small globular micelles, large cylindrical micelles, and spherical vesicles. The characteristics of the aggregates formed are determined by the molecular structure of the surfactant as well as by the solution conditions such as concentration, temperature, ionic strength, and the like.

In certain embodiments, the second surfactant enhances the ability of the first surfactant to form micelles in water. In certain embodiments, the first surfactant comprises a first critical micelle concentration, wherein the combination of the first surfactant and the second surfactant comprises a second critical micelle concentration, wherein the second critical micelle concentration is less than the first critical micelle concentration. In certain embodiments, the first surfactant comprises a first critical micelle temperature, wherein the combination of the first surfactant and the second surfactant comprises a second critical micelle temperature, wherein the second critical micelle temperature is less than the first critical micelle temperature.

In certain embodiments, the first surfactant forms a first micelle comprising a first micellar average molecular weight. The combination of the first surfactant and the second surfactant forms a mixed micelle comprising a mixed micellar average molecular weight, wherein the first micellar average molecular weight differs from the mixed micellar average molecule weight.

In certain embodiments, Applicants' bioavailability enhancement delivery composition further comprises a third surfactant. In certain embodiments, Applicant's third surfactant comprises a cloud point greater than about 37° C. In certain embodiments, Applicant's bioavailability enhancement delivery composition comprises a first surfactant comprising a cloud point greater than about 37° C., a second surfactant comprising a cloud point greater than about 37° C., and a third surfactant comprising a cloud point greater than about 37° C., wherein a mixture of the first surfactant, the second surfactant, and the third surfactant comprises a cloud point less than 37° C.

In certain embodiments, Applicant's third surfactant comprises a triglyceride moiety. In certain embodiments, Applicant's third surfactant comprises an ethoxylated triglyceride. In certain embodiments, Applicant's third surfactant comprises ethoxylated castor oil V.

The reaction product of castor oil and about 30 equivalents of ethylene oxide, i.e. a+b+c=30, comprises a cloud point of about 73° C. (1% in 20% acetic acid). The reaction products of castor oil and between about 30 equivalents to about 60 equivalents of ethylene oxide comprise HLB values of between about 12 to about 15.

Treating castor oil with an excess of ethylene oxide forms a plurality of other compounds in addition to adduct V. Minor components are the polyethylene glycol esters of ricinoleic acid, polyethylene glycols and polyethylene glycol ethers of glycerol. In certain embodiments, Applicant's bioavailability enhancement delivery composition comprises polyethylene glycol esters of various fatty acids, including ricinoleic acid, polyethylene glycols and polyethylene glycol ethers of glycerol.

In certain embodiments, Applicant's bioavailability enhancement delivery composition further comprises a water-insoluble component. In certain embodiments, the water-insoluble component comprises a triglyceride. In certain embodiments, the water-insoluble component comprises a mixture of terpenes. In certain embodiments, the water-insoluble component comprises a mixture of $C_{32}$-$C_{48}$ esters formed from fatty acids and fatty alcohols.

In certain embodiments, the water-insoluble component of Applicant's bioavailability enhancement delivery composition comprises primarily a triglyceride formed from glycerol and ricinoleic acid having structure VI.

In certain embodiments, Applicant's water-insoluble component comprises a plurality of terpenes and terpendoid-type compounds. In certain embodiments, Applicant's water-insoluble component comprises one or more of α-Pinene, Camphene, Myrecene, α-Phellandrane, α-Terpinene, Ocimene, γ-terpinene, Eucalyptol, p-Cymene, 1-octen-3 ol, Tran Sabinen hydrate, Linalool, cis-Sabinen hydrate, α-Campholena, Terpinen-4-ol, Germacrene-D, α-Terpineol, Isoborneol, Cyclohexane, Trans carveol, Carvone, Carvenone, Methyl cinnamate, Thymol, Carvacrol, and α-Cadinol.

The use of polyoxyethylene sorbitan monooleate and tocopheryl polyethylene glycol succinate in combination with a water-insoluble oil to enhance the bioavailability of an API is novel. In fact, Applicant respectfully submits that the prior art teaches away because conventional wisdom would hold that the use of an oil with these surfactants, particularly tocopheryl polyethylene glycol succinate, would saturate them, rendering them useless.

Individually, each of Applicant's two, and optionally three, surfactants will cause at least some dispersion of an API but it is the heretofore unknown mixture of two/three surfactants that creates a microemulsion that increases the bioavailability of an API. Using Applicant's bioavailability enhancement delivery composition, a fine microemulsion is created that enables almost complete API dispersion in water, a result unseen with either of the two surfactants separately or known in the prior art.

In certain embodiments, Applicant's bioavailability enhancement delivery composition comprises surfactants comprising a HLB of between about 12 to about 18. In certain embodiments, Applicant's bioavailability enhancement delivery composition comprises surfactants comprising a HLB of between about 13 to about 16.

In certain embodiments, the weight ratio of polyoxyethylene sorbitan monooleate to tocopheryl polyethylene glycol succinate is between about 1:1 to about 4:1. In certain embodiments, the weight ratio of polyoxyethylene sorbitan monooleate to tocopheryl polyethylene glycol succinate is about 2:1.

In certain embodiments, the weight ratio of oil to surfactant combination is between about 99:1 to about 9:1. Applicant has found that a weight ratio greater than 99:1 do not allow adequate dispersion to take place. Applicant has further found that weight ratio less than about 9:1 cause gelling of the oil:/surfactant combination. In certain embodiments, the weight ratio of oil to surfactant combination is about 12:1.

Applicant has also discovered that certain water-insoluble components, due to their chemical structure, will not disperse in an acceptable manner if added in a one-step process. For these materials, a two-step process is required. For instance, Applicant discovered that oregano essential oil, a mixture of terpenes, cannot be added directly into a mixture Applicant's first surfactant and second surfactant. The mixture of terpenes will not homogeneously disperse, even by adjusting the ratios of the surfactants.

To the mixture of surfactants and optional water-insoluble component is added an API in a therapeutically acceptable amount. In certain embodiments, the API comprises for example and without limitation acetaminophen, atorvastatin, or one or more other APIs.

FIG. 7 summarizes Applicant's method to prepare Applicant's bioavailability enhancement delivery composition. Referring to FIG. 7, in step 710 the method provides a first surfactant and a second surfactant. In certain embodiments, the first surfactant comprises a cloud point greater than about 37° C. In certain embodiments, the first surfactant comprises a HLB value in the range of about 12 to about 18. In certain embodiments, the first surfactant comprises a first critical micelle concentration. In certain embodiments, the first surfactant comprises a first critical micelle temperature. In certain embodiments, the first surfactant comprises polyoxyethylene sorbitan monooleate.

In certain embodiments, the second surfactant comprises a cloud point greater than about 37° C. In certain embodiments, the first surfactant comprises a HLB value in the range of about 12 to about 18. In certain embodiments, the second surfactant comprises tocopheryl polyethylene glycol succinate.

In step 715, the method determines if a mixture of the first surfactant and the second surfactant comprises a cloud point less than about 37° C. If the method determines in step 715 that a mixture of the first surfactant and the second surfactant does not comprise a cloud point less than about 37° C., then the method transitions from step 715 to step 710 and continues as described herein.

If the method determines in step 715 that a mixture of the first surfactant and the second surfactant does comprise a cloud point less than about 37° C., then the method transitions from step 715 to step 720 wherein the method selects an active pharmaceutical ingredient ("API"). In certain embodiments, the API of step 720 is selected from the group consisting of acetaminophen and atorvastatin.

In step 725, the method determines if a third surfactant is desirable. In certain embodiments, step 725 includes determining the solubility of the selected API of step 720 in the mixture of surfactants of step 710. In certain embodiments, step 725 includes varying the weight ratio of the first surfactant to the second surfactant. In certain embodiments, step 725 includes determining a pharmaceutically effective dosage of the API selected in step 720.

If the method determines in step 725 that a third surfactant is not desirable, then the method transitions from step 725 to step 730 wherein the method determines if a water-insoluble component is desirable. In certain embodiments, step 730 includes determining the solubility of the selected API of step 720 in the mixture of surfactants of step 710. In certain embodiments, step 730 includes varying the weight ratio of the first surfactant to the second surfactant. In certain embodiments, step 730 includes determining a pharmaceutically effective dosage of the API selected in step 720.

If the method determines in step 730 that a water-insoluble component is not desirable, then the method transitions from step 730 to step 735 wherein the method forms Applicant's bioavailability enhancement delivery composition by adding a pharmaceutically effective dosage of the API selected in step 720 to a mixture of the first surfactant and second surfactant of step 710.

If the method determines in step 725 that a third surfactant is desirable, then the method transitions from step 725 to step 740 wherein the method selects a third surfactant. In certain embodiments, the third surfactant comprises a cloud point greater than about 37° C. In certain embodiments, the third surfactant comprises a HLB value in the range of about 12 to about 18. In certain embodiments, the third surfactant comprises ethoxylated castor oil.

In step 745, the method determines if a mixture of the first surfactant, second surfactant, and third surfactant comprises a cloud point less than about 37° C. If the method determines in step 745 that a mixture of the first surfactant, second surfactant, and third surfactant does not comprise a cloud point less than about 37° C., then the method transitions from step 745 to step 740 and continues as described herein. If the method determines in step 745 that a mixture of the first surfactant, second surfactant, and third surfactant does comprise a cloud point less than about 37° C., then the method transitions from step 745 to step 730.

If the method determines in step 730 that a water-insoluble component is desirable, then the method transitions from step 730 to step 750 wherein the method selects a water-insoluble component. In step 755, the method determines if the water-insoluble component of step 750 is soluble in a mixture of the first and second surfactant, or if the water-insoluble component is soluble in a mixture of the first surfactant, second surfactant, and third surfactant.

If the method determines in step 755 that the water-insoluble component is soluble in a mixture of the first and second surfactant, or if the water-insoluble component is soluble in a mixture of the first surfactant, second surfactant, and third surfactant, then the method transitions from step 755 to step 760 wherein the method forms Applicant's bioavailability enhancement delivery composition by adding a pharmaceutically effective dosage of the API selected in step 720 to a mixture of the first surfactant and second surfactant of step 710, the optional third surfactant selected in step 740, and the water-insoluble component of step 750.

If the method determines in step 755 that the water-insoluble component is not soluble in a mixture of the first and second surfactant, or if the water-insoluble component is not soluble in a mixture of the first surfactant, second surfactant, and third surfactant, then the method transitions from step 755 to step 765 wherein the method dissolves the water-insoluble component of step 750 in a single one of the surfactants. In step 770, the method adds the mixture of step 765 to the remaining surfactant(s).

In step 775, the method forms Applicant's bioavailability enhancement delivery composition by adding a pharmaceutically effective dosage of the API selected in step 720 to a mixture of the water-insoluble component of step 750, first surfactant and second surfactant of step 710 and the optional third surfactant selected in step 740.

Applicant also discovered that certain APIs, due to their chemical structure, will not disperse fully without the aid of an additional solubilizer. The additional solubilizer can be of any type but the Applicant has discovered that polyethoxylated castor oil, polyethylene glycols, propylene glycol, fatty acids and esters, ethoxylated fatty acids and esters, alcohols, and their derivatives, either singly or in combination, will fully disperse most known APIs. Such additional solubilizer(s) may be added along with the API in any one of step 735 (FIG. 7), 760 (FIG. 7), or 775 (FIG. 7).

Applicant's bioavailability enhancement delivery composition can be utilized in multiple routes of API administration. For example and without limitation, Applicant's bioavailability enhancement delivery composition can be employed in combination with an API administered in a soft gel capsule or in a liquid formulation.

The following example is presented to further illustrate to persons skilled in the art how to make and use the invention. This example is not intended as a limitation, however, upon the scope of the invention, which is defined by the claims appended hereto.

EXAMPLE

Humans subjects were cleared of blood stream detectable levels of Eicosapentaenoic Acid ("EPA") and Docosahexaenoic Acid ("DHA"). Eicosapentaenoic Acid is a 20 carbon, polyunsaturated fatty acid. Docosahexaenoic acid is a 22 carbon, polyunsaturated fatty acid.

Eicosapentaenoic Acid

Docosahexaenoic Acid

The Human subjects were then randomly orally administered a Test Composition, a Purified Fish Oil Composition, or a fish oil-based Prescription Medication, under physician supervision. Applicant's Test Composition comprised 465 milligrams of Eicosapentaenoic Acid, 375 milligrams of Docosahexaenoic Acid, 27 milligrams of Tocopheryl polyethylene glycol succinate, and 52 milligrams of polyoxyethylene sorbitan monooleate. Each capsule comprising Applicant's Test Composition weighed about 1,065 milligrams.

The Test Composition, the Purified Fish Oil Composition, and the Prescription Medication, each comprises the same amounts of DHA and EPA. In addition, the size, weight, and shape of oral dosage of each of the Test Composition, the Purified Fish Oil Composition, and the Prescription Medication, were identical.

EPA, DHA, and the fish oil compositions, comprise one or more "omega-3 fatty acids." N-3 fatty acids, popularly referred to as ω-3 fatty acids or omega-3 fatty acids, are essential unsaturated fatty acids with a double bond (C=C) starting after the third carbon atom from the end of the carbon chain.

Essential fatty acids are molecules that cannot be created by the human body but are vital for normal metabolism. One of the two families of these essential fatty acids is the omega-3 fatty acids. The carbon chain has two ends—the acid (COOH) end and the methyl (CH3) end. The location of the first double bond is counted from the methyl end, which is also known as the omega (ω) end or the n end.

Figure 1:
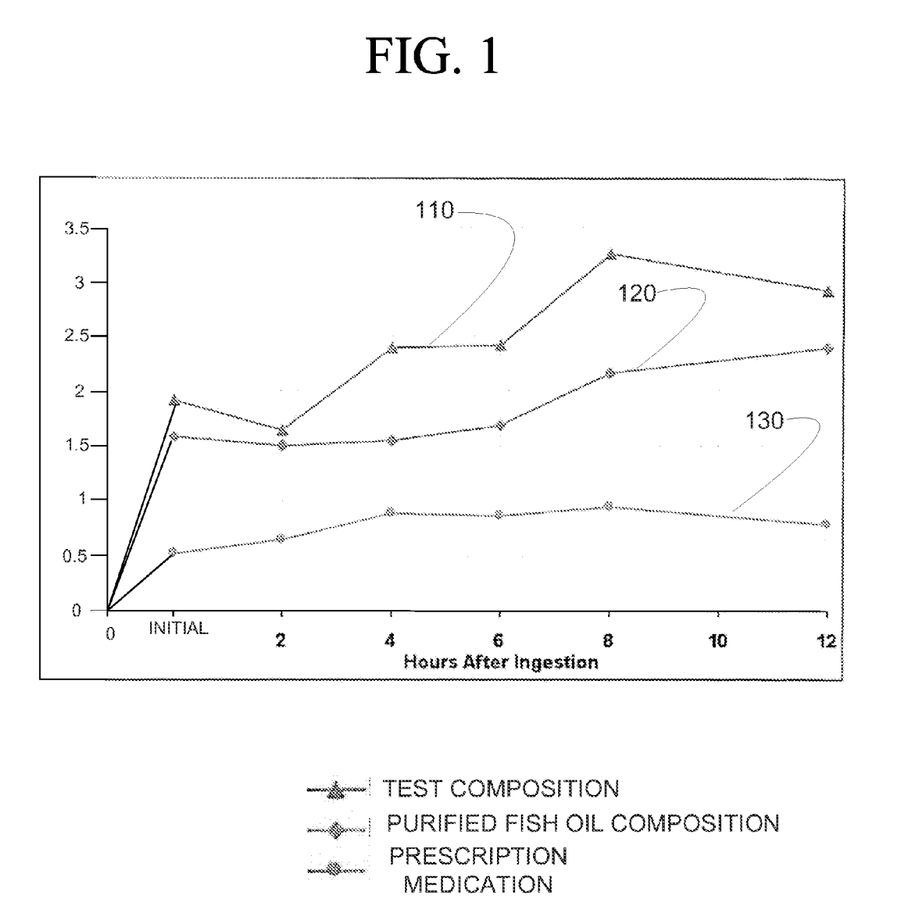
FIG. 1 graphically illustrates average blood level concentrations vs time (Hrs) of Eicosapentaenoic Acid measured in a Test Composition subject group, a Purified Fish Oil subject group, and a Prescription Fish Oil Medication subject group.

Blood samples were obtained from each person in each of the test groups at an INITIAL sampling after administration, and at 2, 4, 6, 8, 10, and 12 hours post oral administration. TABLE 1 recites average blood level concentrations of Eicosapentaenoic Acid determined in each of the three subject groups at each of the time intervals. FIG. 1 graphically illustrates the data of TABLE 1.

TABLE 1

| HOURS AFTER ORAL ADMINISTRATION | TEST COMPOSITION | FISH OIL COMPOSITION | PRESCRIPTION MEDICATION |
|---|---|---|---|
| INITIAL | 1.9 | 1.55 | 0.5 |
| 2 | 1.6 | 1.50 | 0.6 |
| 4 | 2.4 | 1.6 | 0.9 |
| 6 | 2.4 | 1.7 | 0.85 |
| 8 | 3.3 | 2.1 | 0.9 |
| 10 | 3.1 | 2.15 | 0.8 |
| 12 | 2.9 | 2.2 | 0.75 |

Figure 4:
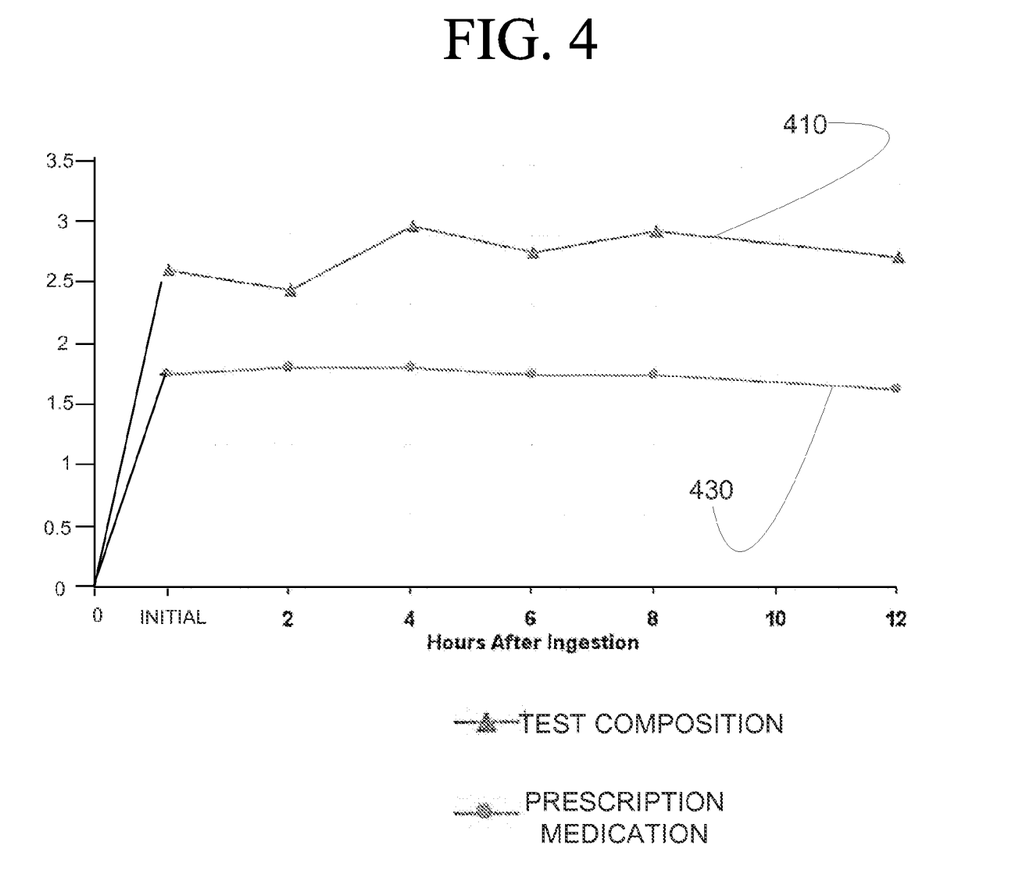
FIG. 4 graphically illustrates average blood level concentrations vs time (Hrs) of Docosahexaenoic Acid measured in a Test Composition subject group, a Purified Fish Oil subject group, and a Prescription Fish Oil Medication subject group.

Referring now to FIG. 1, curve 110 graphically shows the average Docosahexaenoic Acid blood levels measured in the Test Composition subject group. Curve 120 graphically shows the average Docosahexaenoic Acid blood levels measured in the Fish Oil Composition subject group. Curve 430 shows the average Docosahexaenoic Acid blood levels measured in the Prescription Medication subject group. FIG. 4 shows that the Docosahexaenoic Acid blood levels measured in the Test Composition subject group were, at every determination, significantly above those of the Docosahexaenoic Acid blood levels measured in the Prescription Medication subject group.

TABLE 2 recites the rate of average blood level concentration in (mg/dl/hr) of Eicosapentaenoic Acid found in each of the three subject groups. The data of Table 2 shows that the Test Composition had about a four (4) fold faster absorption rate than did the Prescription Medication. The INITIAL blood level data of Table 1 also shows about a four (4) fold faster absorption rate than did the Prescription Medication.

TABLE 2

| TEST COMPOSITION | FISH OIL COMPOSITION | PRESCRIPTION MEDICATION |
| --- | --- | --- |
| 0.253 | 0.10 | 0.06 |

TABLE 3 recites maximum average blood levels in, as Cmax (mg/dl), of Eicosapentaenoic Acid found in each of the three subject groups. The data of Table 3 show that the Test Composition subject group had more than three (3) times the maximum blood level of Eicosapentaenoic Acid compared to the Prescription Medical subject group.

TABLE 3

| TEST COMPOSITION | FISH OIL COMPOSITION | PRESCRIPTION MEDICATION |
| --- | --- | --- |
| 3.27 | 2.62 | 1.00 |

Figure 2:
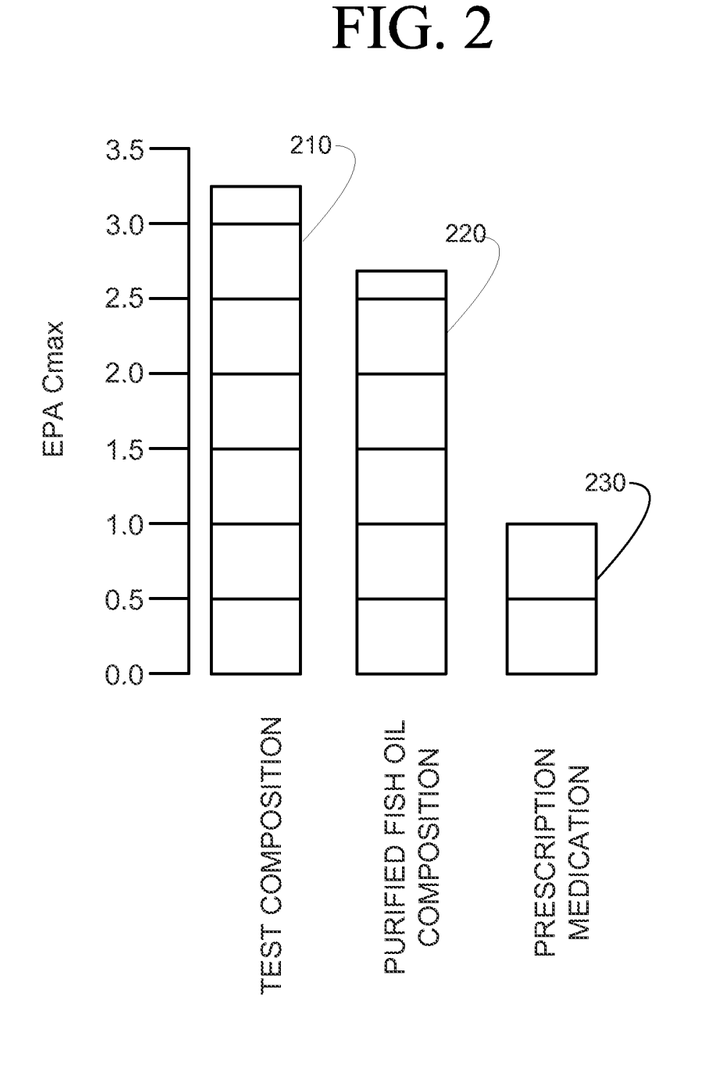
FIG. 2 graphically illustrates maximum Eicosapentaenoic Acid blood level concentrations measured in a Test Composition subject group, a Purified Fish Oil subject group, and a Prescription Fish Oil Medication subject group.

FIG. 2 graphically illustrates the data of TABLE 3. Curve 210 graphically illustrates the average maximum blood level of Eicosapentaenoic Acid found in the Test Composition subject group. Curve 220 graphically illustrates the average maximum blood level of Eicosapentaenoic Acid found in the Fish Oil Composition subject group. Curve 230 graphically illustrates the average maximum blood level of Eicosapentaenoic Acid found in the Prescription Medication subject group.

TABLE 4 recites an integrated area under curve 110 in FIG. 1 corresponding to the measured blood levels of Eicosapentaenoic Acid found in the Test Composition subject group, an integrated area under curve 120 in FIG. 1 corresponding to the measured blood levels of Eicosapentaenoic Acid found in the Fish Oil Composition subject group, and an integrated area under curve 130 in FIG. 1 corresponding to the measured blood levels of Eicosapentaenoic Acid found in the Prescription Medication subject group.

The data of TABLE 4 represent average measured blood levels per hour (mg/dl/hr) found in each of the three subject groups. The data of Table 4 show that the Test Composition subject group had more than three (3) times the aggregate blood level of Eicosapentaenoic Acid compared to the Prescription Medical subject group.

TABLE 4

| TEST COMPOSITION | FISH OIL COMPOSITION | PRESCRIPTION MEDICATION |
| --- | --- | --- |
| 30.40 | 22.30 | 9.70 |

Figure 3:
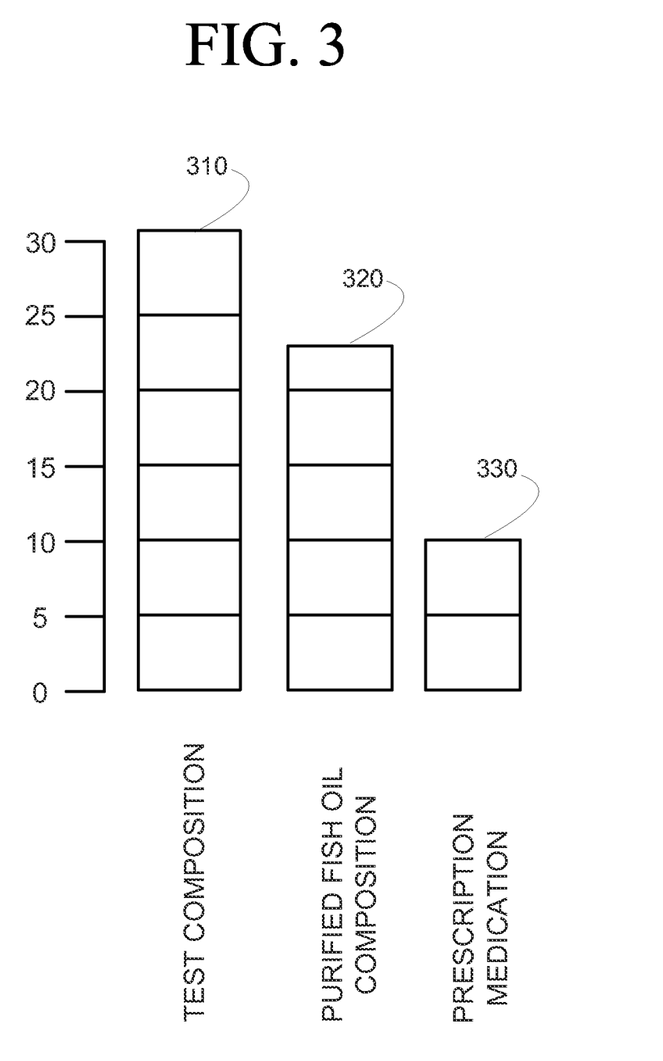
FIG. 3 graphically illustrates aggregate Eicosapentaenoic Acid blood level concentrations measured in a Test Composition subject group, a Purified Fish Oil subject group, and a Prescription Fish Oil Medication subject group.

FIG. 3 graphically illustrates the data of TABLE 4. Curve 310 graphically illustrates an aggregate amount of Eicosapentaenoic Acid measured in blood samples taken from the Test Composition subject group. Curve 320 graphically illustrates an aggregate amount of Eicosapentaenoic Acid measured in blood samples taken from the Fish Oil Composition subject group. Curve 330 graphically illustrates an aggregate amount of Eicosapentaenoic Acid measured in blood samples taken from the Prescription Medication subject group.

TABLE 5 recites average blood level concentrations of Docosahexaenoic Acid at measured at an INITIAL determination after oral administration, and 2, 4, 6, 8, 10, and 12 hours post oral administration for both the Test Composition subject group and the Prescription Medication subject group.

TABLE 5

| HOURS AFTER ORAL ADMINISTRATION | TEST COMPOSITION | PRESCRIPTION MEDICATION |
| --- | --- | --- |
| INITIAL | 4.4 | 3.0 |
| 2 | 4.2 | 3.1 |
| 4 | 5.0 | 3.1 |
| 6 | 4.8 | 2.9 |
| 8 | 5.0 | 3.0 |
| 10 | — | — |
| 12 | 4.9 | 2.9 |

FIG. 4 graphically illustrates the data of TABLE 5. Curve 410 graphically shows the average Docosahexaenoic Acid blood levels measured in the Test Composition subject group. Curve 430 shows the average Docosahexaenoic Acid blood levels measured in the Prescription Medication subject group. FIG. 4 shows that the Docosahexaenoic Acid blood levels measured in the Test Composition subject group were, at every determination, significantly above those of the Docosahexaenoic Acid blood levels measured in the Prescription Medication subject group.

TABLE 6 recites maximum average blood levels in, as Cmax (mg/dl), of Docosahexaenoic acid found in each of the two subject groups. The data of Table 6 show that the Test Composition subject group had more than three (3) times the maximum blood level of Eicosapentaenoic Acid compared to the Prescription Medical subject group.

TABLE 6

| TEST COMPOSITION | FISH OIL COMPOSITION | PRESCRIPTION MEDICATION |
| --- | --- | --- |
| 3.27 | 2.62 | 1.00 |

Figure 5:
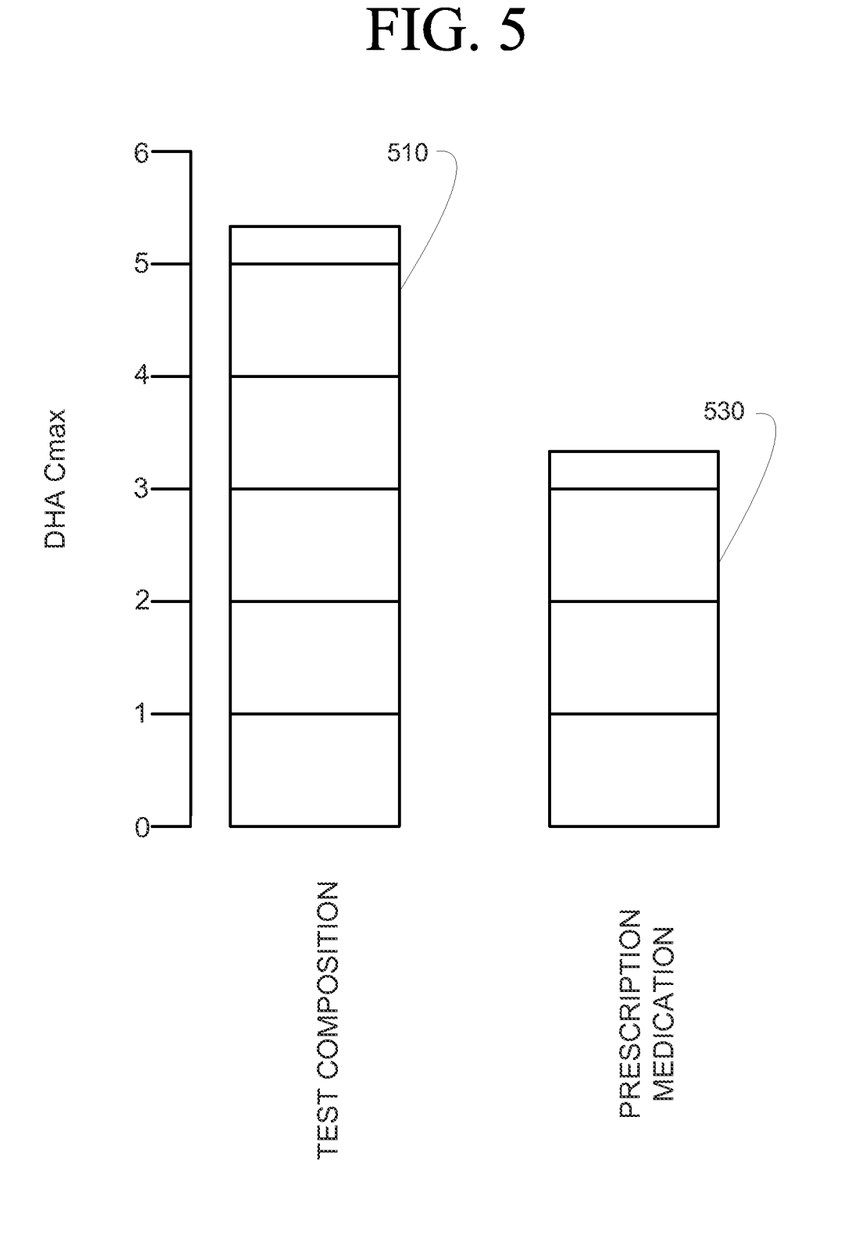
FIG. 5 graphically illustrates maximum Docosahexaenoic Acid blood level concentrations measured in a Test Composition subject group, a Purified Fish Oil subject group, and a Prescription Fish Oil Medication subject group.

FIG. 5 graphically illustrates the data of TABLE 6. Curve 510 graphically illustrates the average maximum blood level of Eicosapentaenoic Acid found in the Test Composition subject group. Curve 530 graphically illustrates the average maximum blood level of Eicosapentaenoic Acid found in the Prescription Medication subject group.

TABLE 7 recites an integrated area under curve 410 in FIG. 4 corresponding to the measured blood levels of Docosahexaenoic Acid found in the Test Composition subject group, and an integrated area under curve 430 corresponding to the measured blood levels of Docosahexaenoic Acid found in the Prescription Medication subject group.

TABLE 7

| TEST COMPOSITION | FISH OIL COMPOSITION | PRESCRIPTION MEDICATION |
| --- | --- | --- |
| 30.40 | 22.30 | 9.70 |

Figure 6:
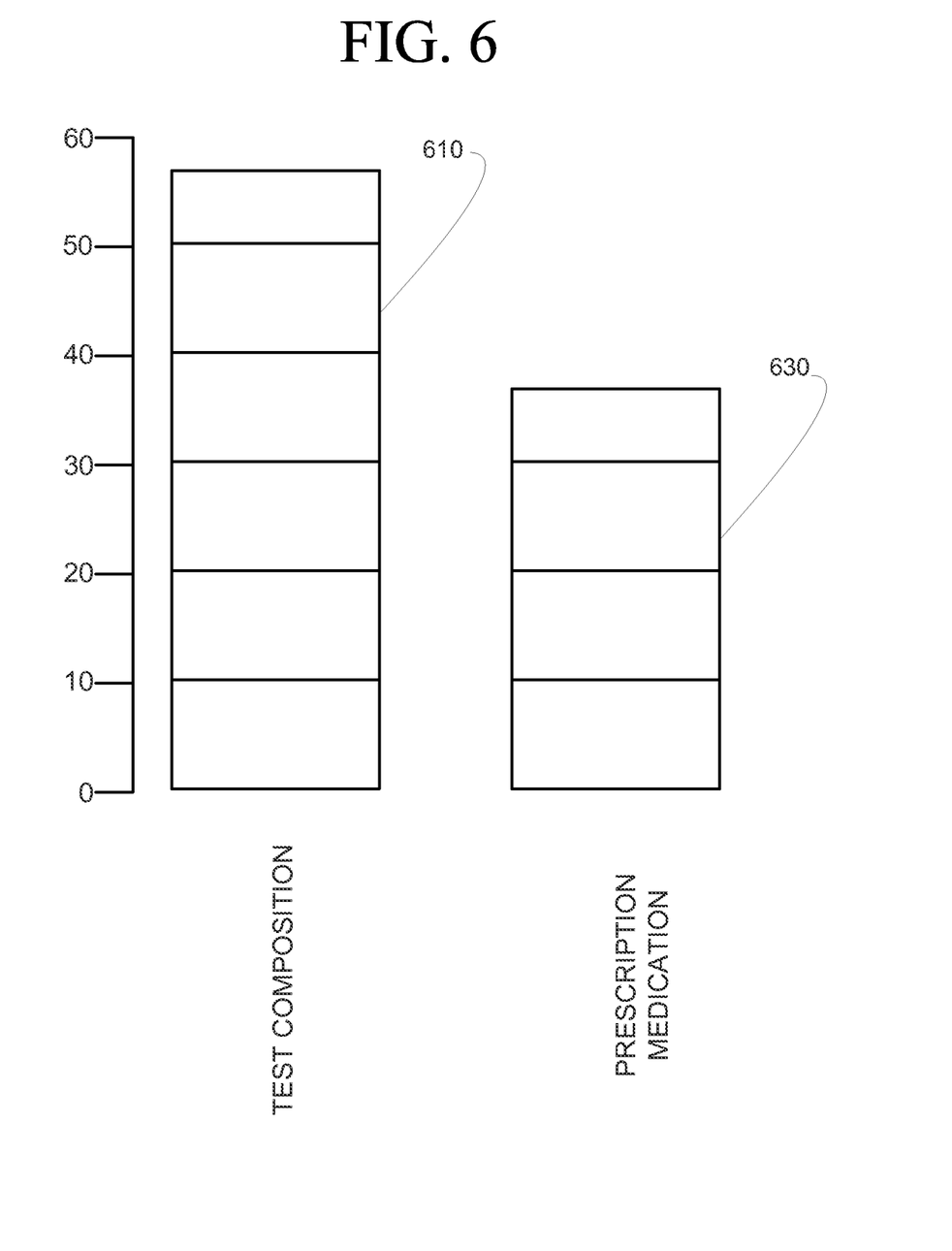
FIG. 6 graphically illustrates aggregate Docosahexaenoic Acid blood level concentrations measured in a Test Composition subject group, a Purified Fish Oil subject group, and a Prescription Fish Oil Medication subject group.

FIG. 6 graphically illustrates the data of TABLE 4. Curve 510 graphically illustrates an aggregate amount of Docosahexaenoic Acid measured in blood samples taken from the Test Composition subject group. Curve 530 graphically illustrates an aggregate amount of Docosahexaenoic Acid measured in blood samples taken from the Prescription Medication subject group.

While the preferred embodiments of the present invention have been illustrated in detail, it should be apparent that modifications and adaptations to those embodiments may occur to one skilled in the art without departing from the scope of the present invention as set forth in the following claims.

I claim:

1. A composition for increasing the bioavailability of an active pharmaceutical ingredient ("API") in humans and animals, consisting of:
   polyoxyethylene sorbitan monooleate having a cloud point greater than about 37° C.;
   tocopheryl polyethylene glycol succinate having a cloud point greater than about 37° C.;
   an API selected from the group consisting of acetaminophen and atorvastatin;
   a terpene;
   wherein a mixture of said polyoxyethylene sorbitan monooleate, said tocopheryl polyethylene glycol succinate, comprises a cloud point less than about 37° C.

* * * * *